(12) United States Patent
Dromerick et al.

(10) Patent No.: US 10,674,943 B2
(45) Date of Patent: Jun. 9, 2020

(54) METHOD AND SYSTEM OF RAPID SCREENING FOR MILD TRAUMATIC BRAIN INJURY (MTBI) AND OTHER COGNITIVE IMPAIRMENT BY ANALYSIS OF INTRA-INDIVIDUAL VARIABILITY OF MOTOR PERFORMANCE

(71) Applicants: Medstar Health Research Institute, Inc., Washington, DC (US); Georgetown University, Washington, DC (US)

(72) Inventors: Alexander Dromerick, Washington, DC (US); Peter S. Lum, Clarksville, MD (US); Rochelle E. Tractenberg, Silver Spring, MD (US)

(73) Assignees: MEDSTAR HEALTH RESEARCH INSTITUTE, INC., Washington, DC (US); GEORGETOWN UNIVERSITY, Washington, DC (US)

( * ) Notice: Subject to any disclaimer, the term of this patent is extended or adjusted under 35 U.S.C. 154(b) by 832 days.

(21) Appl. No.: 14/426,901

(22) PCT Filed: Sep. 6, 2013

(86) PCT No.: PCT/US2013/058567
§ 371 (c)(1),
(2) Date: Mar. 9, 2015

(87) PCT Pub. No.: WO2014/039861
PCT Pub. Date: Mar. 13, 2014

(65) Prior Publication Data
US 2015/0245789 A1    Sep. 3, 2015

Related U.S. Application Data

(60) Provisional application No. 61/698,225, filed on Sep. 7, 2012.

(51) Int. Cl.
*A61B 5/11* (2006.01)
*A61B 5/22* (2006.01)
(Continued)

(52) U.S. Cl.
CPC ............ *A61B 5/1124* (2013.01); *A61B 5/162* (2013.01); *A61B 5/225* (2013.01); *A61B 5/4088* (2013.01);
(Continued)

(58) Field of Classification Search
CPC ....... A61B 5/1124; A61B 5/162; A61B 5/225; A61B 5/4088; A61B 5/18; A61B 2503/10; A61B 5/4064
See application file for complete search history.

(56) References Cited

U.S. PATENT DOCUMENTS 4,885,687 A * 12/1989 Carey ...................... A61B 5/16
                                                              273/440
5,720,711 A *  2/1998 Bond ............... A63B 21/00178
                                                              601/23
(Continued)

OTHER PUBLICATIONS

Stuss et al., Adult Clinical Neuropsychology:Lessons from Studies of the Frontal Lobes, Annual Review of Psychology, 53, 401-433 (2003).
(Continued)

*Primary Examiner* — Rene T Towa
(74) *Attorney, Agent, or Firm* — Tarolli, Sundheim, Covell & Tummino LLP

(57) ABSTRACT

A non-invasive system, and method for simple, quantitative screening for mTBI and other forms of mid cognitive impairment using a visuo-motor performance test (for example, a submaximal grip test) in response to visual feedback to quantitatively measure the intra-individual variability of performance metric for initial screening of patients with mild traumatic brain injury (mTBI), and other neuro-
(Continued)

logical disorders. The system and method can be administered in minutes, by any level of caregiver, in any environment including military in-the-field or sports on-field deployments, and is useful in screening those truly injured from those disguising or mimicking injury. In addition to screening, the system and method can be used to monitor and/or detect changes to intra-individual variability over time by comparison to a baseline, which in turn is helpful in determining estimated recovery trajectory or other related information.

11 Claims, 6 Drawing Sheets

(51) Int. Cl.
*G16H 50/20* (2018.01)
*A61B 5/16* (2006.01)
*A61B 5/00* (2006.01)
*A61B 5/18* (2006.01)

(52) U.S. Cl.
CPC ............... *G16H 50/20* (2018.01); *A61B 5/18* (2013.01); *A61B 5/4064* (2013.01); *A61B 2503/10* (2013.01)

(56) References Cited

U.S. PATENT DOCUMENTS

| | | | | |
|---|---|---|---|---|
| 5,772,611 A * | 6/1998 | Hocherman | ......... | A61B 5/1101 600/595 |
| 6,360,591 B1 | 3/2002 | Carley | | |
| 6,517,480 B1 | 2/2003 | Krass | | |
| 6,613,000 B1 * | 9/2003 | Reinkensmeyer | ..... | A61B 5/221 600/587 |
| 2005/0165327 A1 * | 7/2005 | Thibault | .............. | A61B 3/0066 600/558 |
| 2005/0177065 A1 * | 8/2005 | Ghajar | ................... | A61B 3/113 600/558 |
| 2006/0270945 A1 * | 11/2006 | Ghajar | ................... | A61B 3/113 600/558 |
| 2008/0309616 A1 * | 12/2008 | Massengill | ............ | A61B 3/113 345/156 |
| 2010/0092929 A1 | 4/2010 | Hallowell et al. | | |
| 2010/0113979 A1 * | 5/2010 | Sarrafzadeh | ......... | A61B 5/1107 600/587 |
| 2010/0132058 A1 | 5/2010 | Diatchenko et al. | | |
| 2011/0043350 A1 | 2/2011 | Ben David | | |
| 2011/0137196 A1 * | 6/2011 | Kakei | .................. | A61B 5/0488 600/546 |
| 2011/0144520 A1 | 6/2011 | Causevic et al. | | |

OTHER PUBLICATIONS

Walker et al., Motor Impairment After Severe Traumatic Brain Injury: A Longitudinal Multicenter Study, Jnl of Rehabilitation Research & Development, vl 44, No. 7, pp. 975-982 (2007).

Sosnoff, J.J. et al., Previous Mild Traumatic Brain Injury and Postural-Control Dynamics, Jnl of Athletic Training. 46(1), 85-91 (2011).

Kluger et al., Clinical Features of MCI: Motor Changes, International Psychogeriatrics, Feb; 20(1):32-39 (2008).

Schwab, K. A. et al., Screening for Traumatic Brain Injury in Troops Returning From Deployment in Afghanistan and Iraq: Initial Investigation of The Usefulness of a Short Screening Tool For Traumatic Brain Injury, Jnl of Head Trauma Rehabilitation, 22, 377-389 (2007).

Jamshid Ghajar, The Predictive Brain State: Timing Deficiency in Traumatic Brain Injury?, Neurorehabil Neural Repair; vol. 22 No. 3 217-227, May/Jun. 2008.

Defense and Veterans Brain Injury Center (DVBIC), Acute TBI CPG (2006).

Canadian Office Action for the corresponding Canadian Application Serial No. 2,884,371, dated Jun. 25, 2019, pp. 1-4.

* cited by examiner

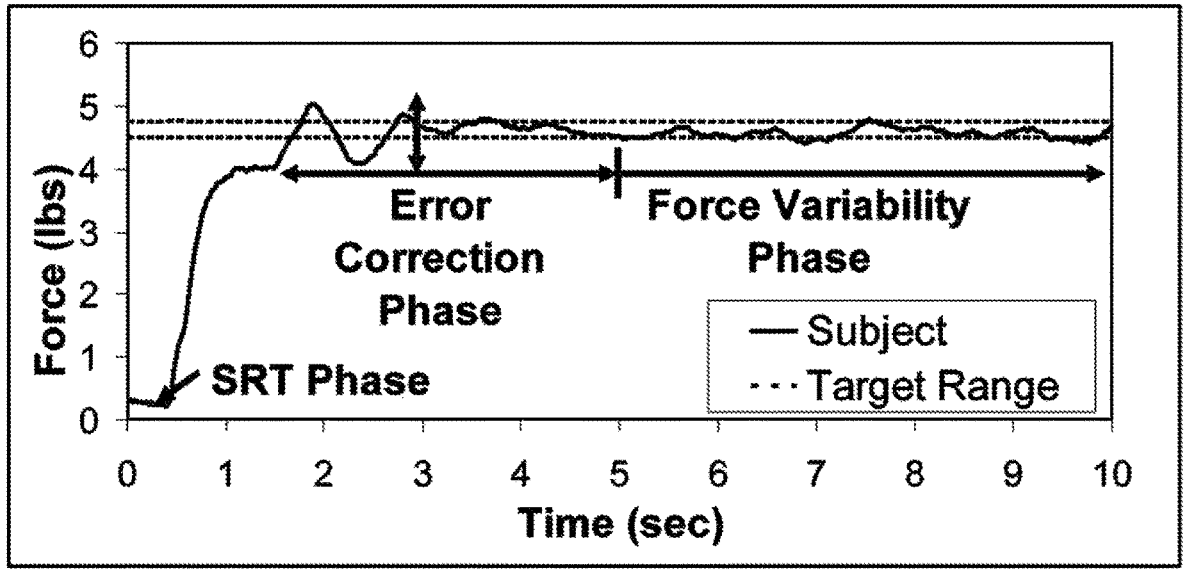

Grip Dynamometry Task Outcomes

FIG. 2

| Table 1: Domains assessed by dynamometry task | | |
|---|---|---|
| Motor Tasks | Cognitive Domain Relevant to TBI | Variable measured by task |
| Simple Reaction Time (SRT) | Psychomotor speed | Reaction time (ms) |
| Error correction | Concentration, self-regulation, novel task performance | Time to achieve desired force (ms) |
| Grip force variability | Sustained attention, consistency of performance, fatigability | Variability of force (lbs, mean ± SD) |

FIG. 3

METHOD AND SYSTEM OF RAPID SCREENING FOR MILD TRAUMATIC BRAIN INJURY (MTBI) AND OTHER COGNITIVE IMPAIRMENT BY ANALYSIS OF INTRA-INDIVIDUAL VARIABILITY OF MOTOR PERFORMANCE

STATEMENT OF GOVERNMENT INTEREST

The invention was supported, in whole or in part, by The Telemedicine & Advanced Technology Research Center (TATRC), which is an office of the headquarters of the US Army Medical Research and Materiel Command (USAM-RMC). The U.S. Government has certain rights in the invention.

BACKGROUND OF THE INVENTION

1. Field of the Invention

The present invention relates to clinical screening techniques for identifying cognitive impairment and, more particularly, to a non-invasive system and method for quantitative screening for mild traumatic brain injury (mTBI) and other neurological disorders by evaluating the intra-individual variability (IIV) of motor performance.

2. Description of Prior Art

In many activities, overall performance is dependent on a high level of cognitive performance. However, there are certain forms of mild cognitive impairment (MCI) that can compromise performance, including mild traumatic brain injury (mTBI), early Alzheimer's disease, post-traumatic stress disorder (PTSD), intoxication, and sleep deprivation.

mTBI is particularly common in the military and athletic settings. The onset of mTBI is very subtle, and yet it can have serious consequences if left undetected and untreated. Detecting mTBI is very difficult because the symptoms are not always manifest. An individual may be superficially functioning quite well day-to-day, continuing to work, and apparently not restricted in any daily activity. Moreover, individuals exhibit different signs and symptoms, the functional consequences appear gradually, and no specific test has been developed for diagnosis. The gold standard method of assessing mTBI is to perform a detailed neurological evaluation, extensive cognitive testing, and imaging. This traditional approach imposes undesirable costs and delays and is impractical on the playing field, battle field (for forwardly deployed military personnel), or on the jobsite. Consequently, in some situations there is a significant need to screen individuals for mild cognitive impairment to ensure that they are capable of performing certain tasks safely without risk to themselves or others, or that a degenerative condition does not exist.

The armed services in particular have a long-felt need to assess mild traumatic brain injury (mTBI) which can arise from injuries by explosions or the like or from PTSD. The cognitive and motor hallmarks of mTBI include psychomotor slowing, poor concentration and attention retrieval resulting in increased variability of performance, and overall executive dysfunction. Stuss et al., *Adult Clinical Neuropsychology: Lessons from Studies of the Frontal Lobes*, Annual Review of Psychology, 53, 401-433 (2003). Previous work has shown that these features are manifest in both cognitive function and motor performance, reaction time and performance reliability. Walker et al., *Motor Impairment After Severe Traumatic Brain Injury: A Longitudinal Multicenter Study*, Jnl of Rehabilitation Research & Development, vl 44, no. 7, pp 975-982 (2007). Also, Sosnoff, Broglio & Ferrara suggest that mTBI reduces motor control especially when visual information is utilized. Sosnoff, J. J. et al., *Previous Mild Traumatic Brain Injury And Postural-Control Dynamics*, Jnl of Athletic Training. 46(1), 85-91 (2011). Furthermore, clinical motor/psychomotor evaluations (tests of balance and coordination) are sensitive to mild cognitive impairment. See, e.g., Kluger et al., *Clinical Features of MCI: Motor Changes*, International Psychogeriatrics, February; 20 (1): 32-39 (2008). Work-related manifestations include slower reaction time, headaches, irritability, memory impairments, and sleep difficulty. These symptoms result in decreased performance of far-forward troops, where performance is critical to mission effectiveness and safety. The military seeks to assess this not only to determine who has sustained an injury, but also their recovery trajectory in order to predict return to duty, and also to detect malingering by those who feign mTBI to gain an early discharge. As a result, there is a major cognitive assessment initiative for Service Members. In 2008 the Assistant Secretary of Defense, Health Affairs office, directed all Services to begin implementing baseline pre-deployment neurocognitive assessments for all Service members. Their original goal was to establish a baseline in the event that the Service member becomes injured or is exposed to a traumatic brain injury (TBI), so that subsequent test results can be compared to the original baseline to determine the extent of MCI and treatment options. An automated tool was developed to collect the baseline information on attention, memory, and thinking ability. The tool, the Automated Neuropsychological Assessment Metrics (ANAM®) test system consists of a library of computer-based tests that include neuropsychology, readiness to perform, neurotoxicology, pharmacology, and human factors research. Other neuropsychological tests include the Trail Making Test (a paper and pencil test in which the subject is instructed to connect a set of 25 dots as fast as possible while still maintaining accuracy), screening interviews such as the Military Acute Concussion Evaluation (MACE), and computerized cognitive tests such as the Automated Neuropsychological Assessment Metrics (ANAM), ImPACT, and a variety of other computerized tests. The existing MACE screening tool and the ANAM battery are the current assessments used to evaluate mTBI. Defense and Veterans Brain Injury Center (DVBIC), *Clinical Practice Guidelines and Recommendations*, Working Group on the Acute Management of Mild Traumatic Brain Injury in Military Operational Settings (2006). Both tools represent the culmination of years of work by the military. Schwab, K, A. et al., *Screening For Traumatic Brain Injury In Troops Returning From Deployment In Afghanistan And Iraq: Initial Investigation of The Usefulness of a Short Screening Tool For Traumatic Brain Injury*, Jnl of Head Trauma Rehabilitation, 22, 377-389 (2007). However, both tools take considerable time and require professionally trained testers. The deficiencies in the sensitivity and specificity of these tests to mTBI have been well documented.

More recently, it has been suggested that mTBI affects attention and impairs the anticipatory process. There is a distinct relationship between attention and motor performance variability. Specifically, mTBI patients show an increase in the degree to which their performance varies from trial to trial. Jamshid Ghajar, *The Predictive Brain State: Timing Deficiency in Traumatic Brain Injury?*, Neurorehabil Neural Repair May/June 2008 vol, 22 no. 3 217-227.

Although it is currently possible to measure and monitor motor performance variability in a clinical setting, there is no existing standardized method or system for doing so in the field. Therefore, military medical specialists and other far-forward personnel have no means to assess mTBI. The present inventors have developed a method and system to assess intra-individual response variability (IIV) as manifested in a simple motor task (for example, tracking visual targets) that is an effective mTBI screen and, either alone or in combination with one or more other assessments, potentially a test for diagnosing mTBI or other cognitive impairments such as brain damage, concussion and/or dementia. It is also directly relevant to the athletic setting, and settings where sleep deprivation or intoxication may require detection. The proposed method and system is simple, quantitative, noninvasive, and suitable for use in any environment by any personnel at all echelons of care.

SUMMARY OF THE INVENTION

It is an object of the present invention to provide a system and method for reliably discriminating subtle cognitive impairment due to causes such as mild traumatic brain injury (mTBI) from normal controls by a quantitative measure of intra-individual variability (IIV) of motor performance.

It is another object to provide a system and method for quantitative screening for mTBI based on robust metrics that eliminate or reduce the need for pre-injury or baseline data.

It is another object of the present invention to provide a non-invasive system and method for simple, quantitative screening for subtle cognitive impairment due to mTBI and other causes by administration of a test of visuo-motor performance, measurement of intra-individual variability (IIV) from said test, and analysis thereof.

It is another object to provide a system and method for mTBI screening that can be administered in minutes, by any level of caregiver, in any environment including military and sporting field deployments.

It is still another object to provide a screening system and method for subtle cognitive impairment due to mTBI and other causes that collects quantitative data useful in distinguishing between those truly injured and those disguising or mimicking injury.

These and other objects are accomplished by a non-invasive system and method for simple, screening for mTBI using a quantitative measure of intra-individual variability of visuo-motor performance (motor test in response to visual feedback). A preferred embodiment is disclosed in which submaximal grip tests are administered to an individual using a hand dynamometer with load cell transducer outputting digital grip force data to a computer or mobile computing device (e.g. mobile phone, tablet computer or stand-alone device). The computer (or mobile device) runs software including a patient interface for graphically guiding the individual through two experimental visuomotor tasks: 1) tracking a predictable visual target; and 2) tracking an unpredictable visual target, both measuring the individual's fine visuomotor tracking accuracy (as opposed to reaction speed) in response to a stimulus on a computer screen (there is not a direct correlation between tracking accuracy and reaction speed, but reaction speed does contribute to accuracy). The software includes an analysis software module for interpreting, analyzing and displaying test results. The patient interface provides visual cues to the individual to position a cursor (by adjusting their grip continuously to vary grip force) relative to a target. In the predictable task, the target moves in a predictable pattern at a predictable rate. In the unpredictable task, the target moves in an unpredictable pattern and/or at an unpredictable rate. These data are collected and analyzed to compute measures of intra-individual variability of performance. Individuals whose intra-individual variability exceeds a pre-specified threshold can then be referred for further evaluation. The system and method has great utility for initial screening of individuals showing signs of dysfunction from mTBI, and can potentially be used for screening other cognitive impairments such as brain damage, concussion, dementia, sleep deprivation, intoxication and the like. In addition to screening, the system and method can be used for ongoing monitoring by comparison of the intra-individual variability metrics to a baseline over time, e.g., to detect changes over time. The quantified changes over time can then be used for analysis of time-dependent parameters, such as a patient's estimated recovery trajectory or return-to-duty decimaking.

In this context the system and method can be administered in minutes, by any level of caregiver, in any environment including military or athletic field deployments, and is useful in screening those truly injured from those disguising or mimicking injury. Moreover, the system and method may potentially be used alone or in combination with one or more other assessments as a test for diagnosing mTBI or other cognitive impairments.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 2 is a plot for comparative purposes of a grip test dynamometry sequence for a motor constancy test (imposition and maintenance of a stationary target grip force) in terms of force as a function of time.

FIG. 3 is a table of the fine motor performance metrics obtainable from a motor constancy test as in FIG. 2.

DETAILED DESCRIPTION OF THE PREFERRED EMBODIMENTS

The present invention is a non-invasive system and method for simple, quantitative screening for mild cognitive impairment due, for example, to post traumatic stress disorder (PTSD), mild traumatic brain injury (mTBI), and other neurological disorders. The invention relies on a quantitative measure of intra-individual variability of motor performance for the screening.

For purposes of the present application a "screen" is a diagnostic test designed to identify individuals having an increased risk of the disorder, but typically does not provide a clinical diagnosis. The invention is proven effective as a screening tool for mTBI, and shows promise in screening other cognitive impairments such as brain damage, concussion, sleep deprivation, intoxication and the like. Moreover, the invention may potentially be used alone or in combination with one or more other assessments for positively diagnosing mTBI or other cognitive impairments.

Figure 1:
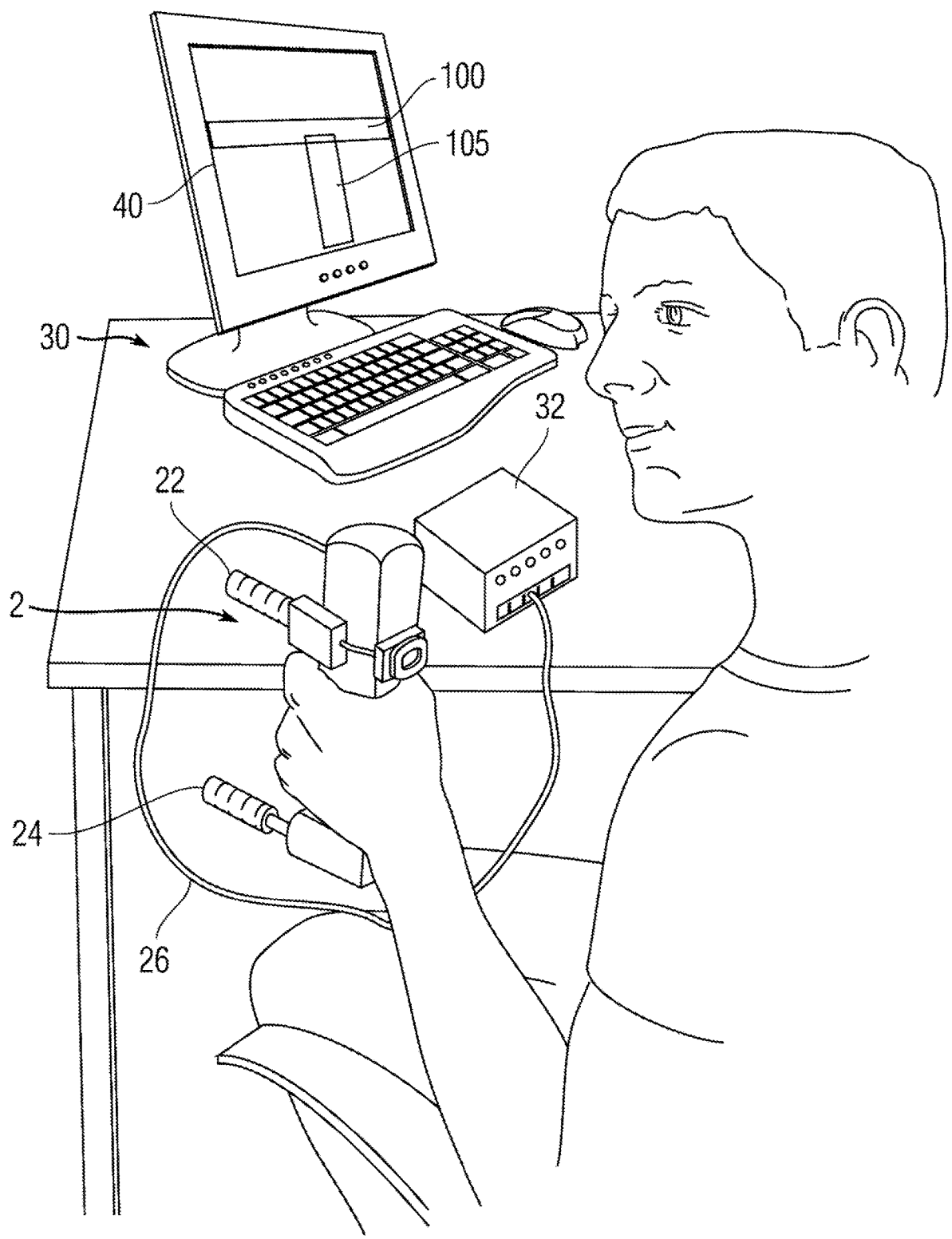
FIG. 1 shows a system for quantitative screening for cognitive impairment according to an exemplary embodiment of the present invention.

FIG. 1 is a perspective view of an exemplary embodiment of the system implemented with a grip test for establishing motor performance metrics, which generally employs a hand dynamometer 2 containing a transducer that generates digital grip-strength data that can be read into a computer. Hand dynamometer 2 may be mechanically similar to a Jamar® dynamometer which comprises two offset parallel bars 22, 24 that can be situated at various preset positions to accommodate various hand sizes. A subject is asked to squeeze the offset parallel bars 22, 24 of the device. However, unlike the Jamar® where the highest force exerted is measured and displayed on a mechanical gauge, the transducers of the present invention comprise one or more digital load cells which output digital grip-strength data via cable 26 to a programmable data acquisition unit 32.

In an embodiment, hand dynamometer 2 may also be equipped with supplemental sensors for providing various other types of feedback, for example an accelerometer such as a MEMS 3-axis motion sensor for monitoring orientation and linear movement of the hand dynamometer 2. The combined digital grip force signals plus those from supplemental sensors are fed to the data acquisition unit 32 and stored, and transferred in real-time or later to Host PC 30. Data acquisition unit 32 serves two primary functions: 1) data recording; plus 2) the ability to multiplex various sensor signals together for recording. The data acquisition unit 32 may be connected to a host PC 30 via a cable, or alternatively, during recording the data may be stored on a flash memory card in data acquisition unit 32, which is later removed and inserted into host PC 30 for importing data into the software of the present invention.

Host PC 30 may be a common laptop or desktop computer or other processing device running software for implementing the method of the present invention. The Host PC 30 runs software comprised of two software modules: 1) a display and analysis software module for interpreting, analyzing and displaying test results to healthcare providers; and 2) a patient/user interface that presents the predictable and unpredictable grip strength/target-tracking variability tests made interactive by the hand dynamometer 2, similar to a video game. Thus, display device 40, in this instance the LCD video display of desktop computer 30, displays a graphical user interface that guides the user through at least two motor performance tests based on assessment of intra-individual variability of grip strength; under both predictable and un-predictable conditions. The tests may include any of a variety of simulations, all preferably requiring a submaximal grip.

FIG. 1 includes an illustration of an exemplary visuomotor tracking test presented by patient user interface. This exemplary tracking test comprises a horizontal band 100 that moves up and down the display 40. The subject controls the height of a vertical band 105 by the amount of grip force exerted to hand dynamometer 2, raising band 105 with more force and lowering with less. The patient user interface instructs the subject to keep the tip of band 105 aligned with band 100. In the predictable test, the subject is informed, of the predictable nature and band 100 moves up and down the display 40 in a predictable pattern (e.g., a constant repeating cycle). In the unpredictable test, the subject is informed of the unpredictable nature, and band 100 moves up and down the display 40 in an unpredictable pattern. Most any unpredictable pattern will suffice in which some aspect of the target band 100 moves in an irregular pattern (e.g., varying speed, frequency, sporadic reversals, etc.). A pseudo-randomly-generated computer pattern will suffice, though for present purposes any pattern may be employed in which the movement of target icon is, at least in one aspect, presented to the patient in a non-repetitive manner. Although the illustrated embodiment entails a simple moving band 100, one skilled in the art should understand that the same data can be gleaned from a wide variety of visual prompts, some more engaging, virtually any target-tracking scenario will suffice in which the subject manipulates an on-screen icon to track a moving target, the target moving at a controlled rate and/or pattern. Other non-tracking visual prompts may also suffice, such as an arcade claw game in which the user must manipulate a claw and maintain a sustained submaximal grip to pick up and move something without dropping or damaging it. The patient user interface presents visual feedback, and so the goal is to prompt the patient to respond to a visual stimulus on display device 40 by applying grip force to the hand dynamometer 2.

Preferably, the target grip force is within a range of from 5-50% of age-matched normalized maximum grip strength, and most preferably approximately 5%+/−0.25 pounds. This ensures that muscle fatigue does not occur, and the continuous submaximal motor effort emphasizes the roles of sustained attention and consistency of performance. This sustained submaximal grip test results in three distinct and measurable phases of the grip, as follows.

FIG. 2 is a plot for comparative purposes of a grip test dynamometry sequence for a motor constancy test (imposition and maintenance of a stationary target grip force) in terms of force as a function of time. From the time that the subject applies their grip (in response to a visual stimulus on computer 30), the first phase is a measurable simple reaction time (SRT) phase. Shortly after the grip is applied the subject strives to adjust it (again in response to visual stimuli on computer 30) in order to achieve the proper level of submaximal force. This second phase is the error correction phase. Finally, the subject must maintain the target grip force for four minutes, and this is known as the grip force variability phase. Each of these phases yields one or more metrics potentially useful for screening purposes, as shown in the table of FIG. 3. For example, the Simple Reaction Time (SRT) correlates to both psychomotor speed and reaction time (ms). Error correction correlates to concentration, self-regulation, and novel task performance. Grip force variability correlates to sustained attention, consistency of performance, and fatigability. The present inventors have found that intra-individual grip force variability presents the strongest correlation, and yet still does not adequately discriminate between mTBI and control subjects in the context of motor constancy tasks. The present inventors introduce a more discriminating visuomotor task, in two-dimensions (predictable versus unpredictable), which combine to provide a more discriminating metric, intra-individual variability of visuomotor response to a dynamic target. The present invention provides an effective field-deployable computerized, system and method for measuring and analyzing the metric.

Figure 4:
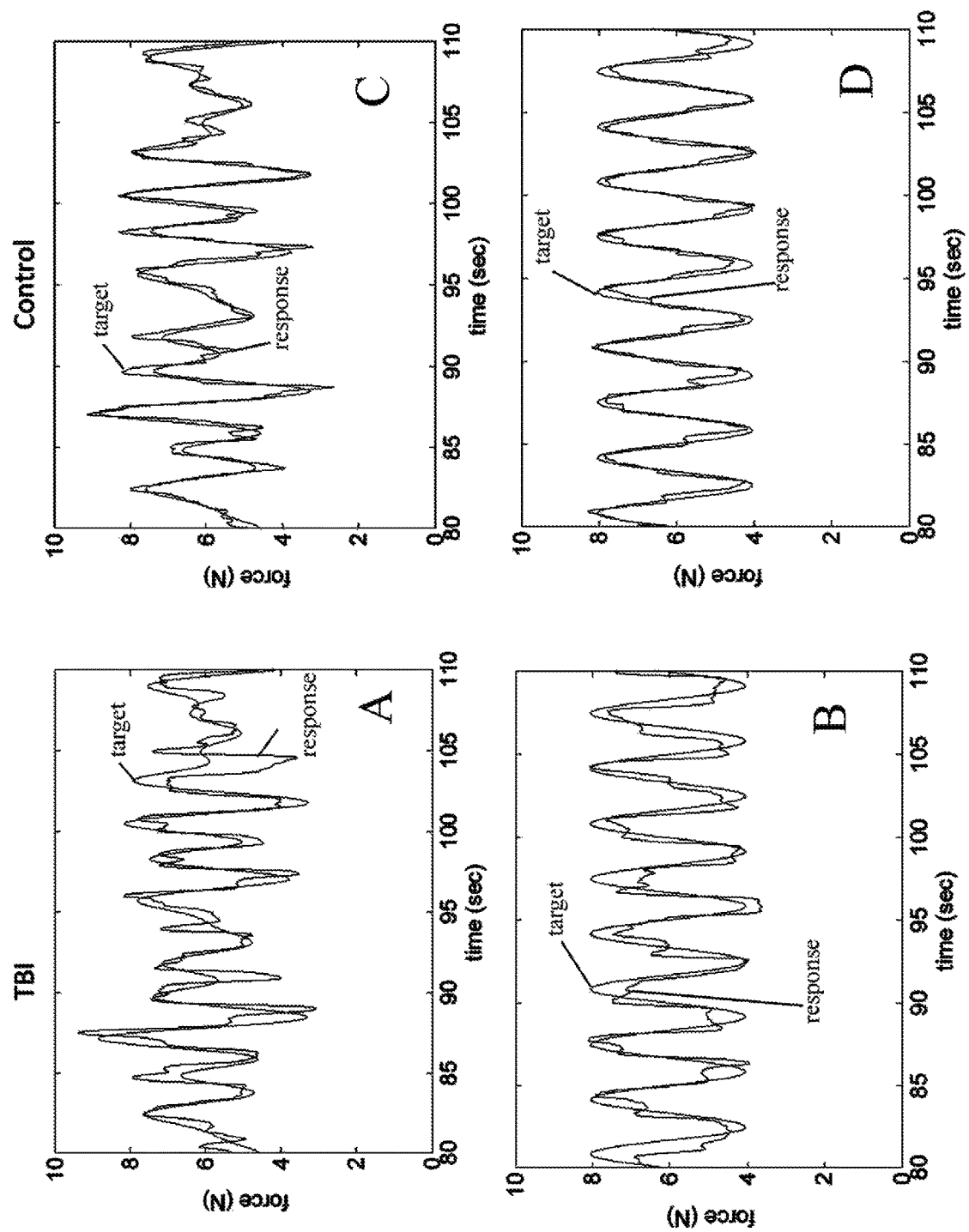
FIG. 4 is a chronological plot of a grip test dynamometry sequence in terms of force as a function of time for the dynamic motor test of the present invention, using the dynamic tracking test of FIG. 1

FIG. 4 is a chronological plot of a grip test dynamometry sequence in terms of force as a function of time for the dynamic motor test of the present invention, using the dynamic tracking test of FIG. 1 in which the horizontal band 100 (FIG. 1) is moved up and down the display 40 at a predictable rate in a predictable (sinusoidal) pattern for known mTBI subjects (B) versus a control group (D), and in which in which the horizontal band 100 is moved up and down the display 40 at an unpredictable rate in an unpredictable pattern for known mTBI subjects (A) versus a control group (B). The target pattern and response is designated. In this example, the patient user interface instructed the subject to grip the device 2 and keep the tip of band 105 inside band 100. The patient user interface also instructed the subject whether the pattern would be predictable or not. In the predictable test, band 100 was moved up and down the display 40 for a total of three minutes pursuant to a predictable sine wave up/down pattern and rate. In the unpredictable test, band 100 was moved up and down the display 40 for a total of three minutes pursuant to a pattern comprising three superposed sine waves, which result in a varying up/down pattern and rate. Thirteen known mTBI subjects were tested along with thirteen control subjects. The plot (FIG. 4) roughly indicates that dynamic tracking tests result in a larger intra-individual variability for mTBI subjects than the control group making it possible to discriminate between mTBI and control subjects.

Figure 5:
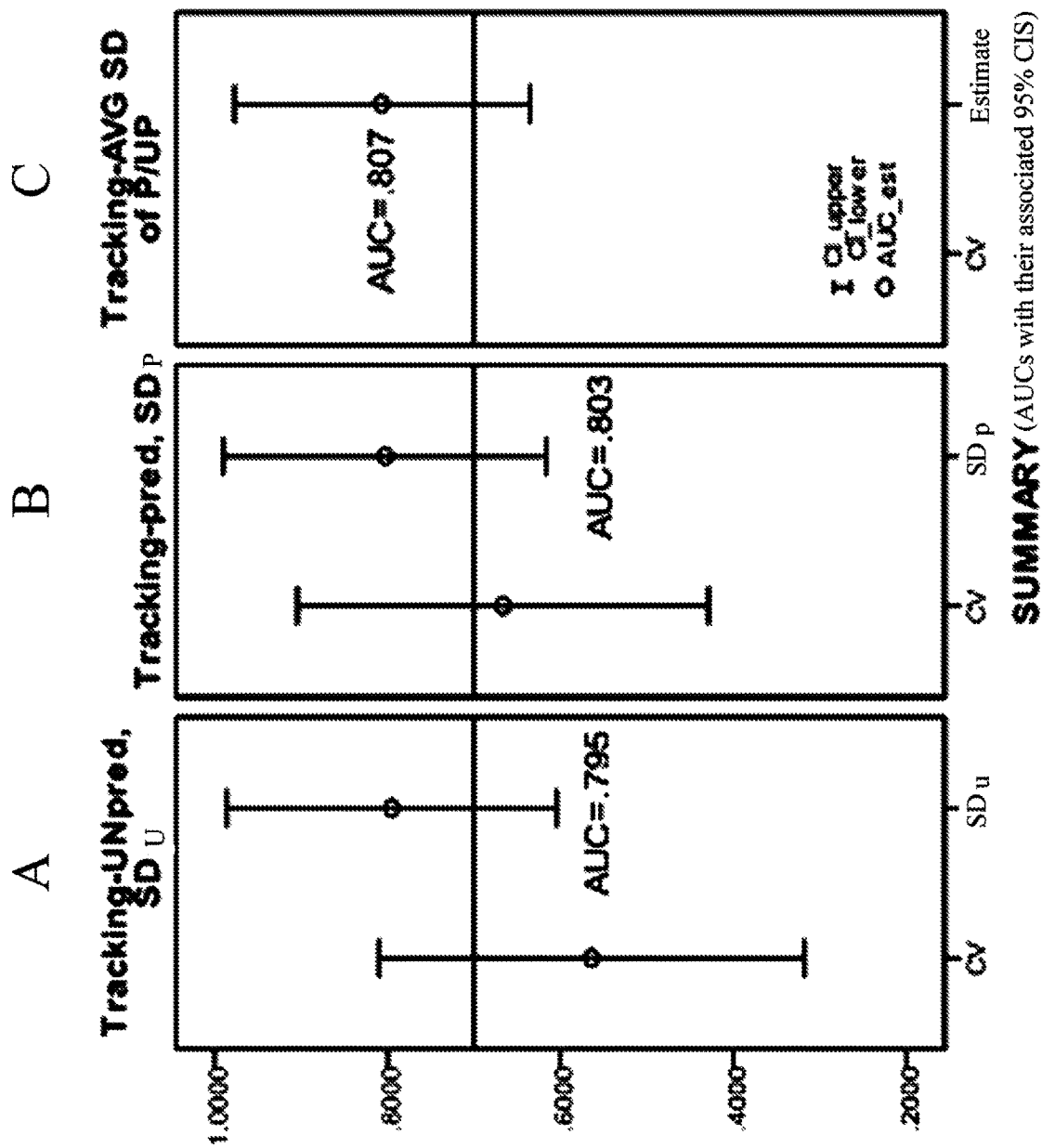
FIG. 5 is a graphical illustration of an exemplary software method for quantifying the intra-individual variability in response to a dynamic target as in FIG. 4

FIG. 5 is a graphical illustration of an exemplary software method for quantifying the intra-individual variability in response to a dynamic target as in FIG. 4, suitable for use by the display and analysis software module of Host PC 30.

Initially, the grip test dynamometry sequence captures force as a function of time for both unpredictable and predictable tracking tasks. The software computes the individual's standard deviation (SD) relative to their mean force over each task, which provides a measure of visuomotor variability. As seen at FIG. 5A-B, the standard deviation (SD) relative to mean force is computed separately for predictable (at B) and unpredictable (at A) tasks ($SD_P$ and $SD_U$, respectively). The SD can be summarized as a function of the individual's mean, using the coefficient of variation (CV) or simply as the standard deviation (SD) itself over the task for the individual, and both metrics are shown in both of FIGS. 5A, B. Performance of the predictable and unpredictable tasks to discriminate patients from controls may be summarized as the area under the curve (AUC) derived from receiver operant characteristic (ROC) curves. These AUC estimates, together with their 95% confidence intervals, are reflected in FIG. 5. In FIG. 5C the $SD_P$ and $SD_U$ summaries (from FIGS. 5A,B) from the predictable and unpredictable tracking tasks were averaged together for each individual, and ROC curves were used to generate the AUC estimate (AUC est) and associated confidence interval (CL upper and CL lower) shown in FIG. 5C. The AUC estimates provide an indication as to whether the averaged $SD_P$ and $SD_U$ summaries are useful for distinguishing patients and controls. Thus, for FIG. 5C the AUC estimate of 0.807 is compared to chance (0.50), or to the best the ANAM can do (0.79). Thus, the illustrated AUC estimate of 0.807 means that 80.7% of the time, the average of SDs from one individual's predictable and unpredictable tracking task performances will correctly label them as "possibly injured" or "probably not injured", and this metric in combination with the average of SDs serves as an exemplary software criterion for screening individuals. Actual test results have confirmed that the above-described system and method are superior to the conventional ANAM tests in discriminating mTBI from controls. In further testing with control groups conditioned to replicate malingering (intentionally portraying mTBI), the test results are able to discriminate malingering from actual mTBI.

Figure 6:
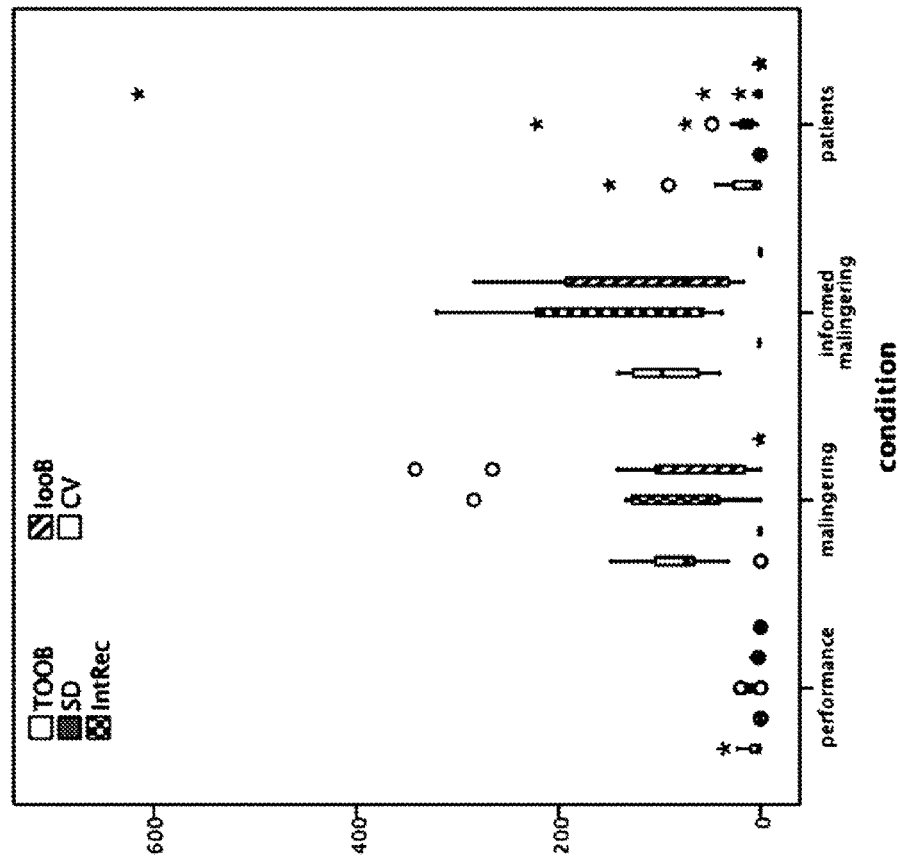
FIG. 6 is a graph illustrating distributions of group performance including normal performance, naïve performance and informed malingering, versus distributions of patients' performance ((far right).

FIG. 6 is a graph illustrating distributions of group performance on the motor constancy task, summarized in five different (cross-validating) ways for each of three conditions all done by the same control participants: normal ("performance"), naïve malingering ("malingering") and informed malingering. The five different ways include the following statistical analyses on the datasets available with MATLAB™ and Statistics Toolbox™:

standard deviation (SD): measure of individual's standard deviation for force exerted from the mean;
coefficient of variation (CV): individual's standard deviation divided by average;
IntRec: integrated rectified difference approximation;
TOOB; time out of bar;
ISD—individual's SD for force exerted.

The single condition performed by patients (far right) is included to demonstrate the pronounced differences between control normal performance and their malingering performances, and between malingering and patients' performance.

Figure 7:
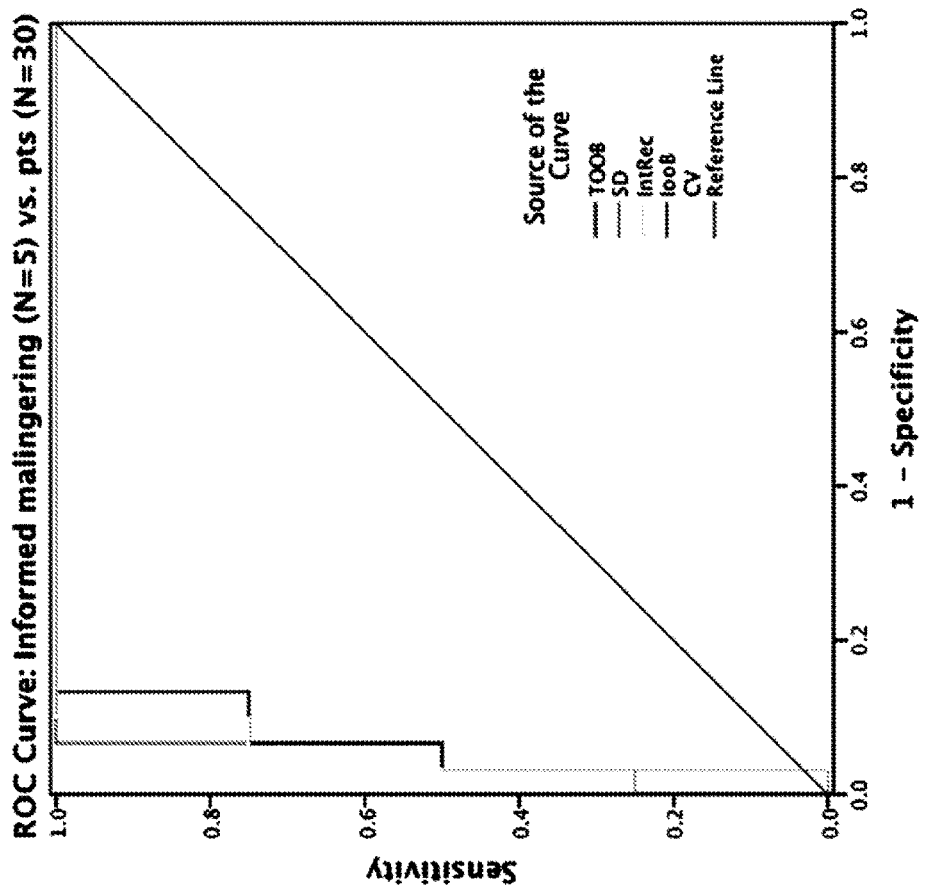
FIG. 7 is a graph illustrating dramatic ROC curves showing informed malingering (N=5) clearly distinguishable from patients (N=30).

FIG. 7 is a graph illustrating dramatic ROC curves showing informed malingering (N=5) clearly distinguishable from patients (N=30). This ROC graph summarizes the performance of the motor constancy task, summarized in the five different ways, for distinguishing control participants' informed malingering (N=5) from patients (N=30).

One skilled in the art should understand that the present invention may employ quantitative measures of intra-individual variability using other motor performance tasks, and that a grip test using hand dynamometer 2 is not the only conceivable means for accomplishing the present invention. For example, a pinch task using a pressure transducer to derive a quantitative measure of variability of pinch pressure will also suffice, or any other pressing or pressure-oriented task, finger tapping task or dexterity test, or other task-oriented evaluation of motor performance may suffice for the screening given the appropriate transducer(s) in an appropriate mechanical construct, as a matter of design choice.

The foregoing intra-individual dynamic visuomotor metrics are measured, analyzed and stored in the data acquisition unit 32 and/or computer 30 and may be used both for initial screening and ongoing evaluation of patients with mild traumatic brain injury (mTBI), and possibly other neurological disorders.

The screening takes just a few minutes and is most expedient for identifying forwardly deployed military personnel who have suffered mTBI through blast or other causes. This approach of using a dynamic-tracking motor task to generate quantitative neurophysiological data, and then screening that data for cognitive impairment helps get individuals that likely have mTBI into treatment sooner. Conversely, it avoids unneeded transport of patients or athletes that likely do not have mTBI for clinical evaluation. The present diagnostic test may be synergistically combined with one or more other assessments, potentially to diagnose mTBI or other cognitive impairments such as brain damage, concussion and/or dementia. For example, in conjunction with the ANAM test, the positive predictive value of the latter would increase because this more comprehensive test is used on a more selected population, reduced by prescreening. The same principal holds true for other combinations, e.g., with a breathalyzer test for alcohol impairment.

In addition to screening, the present diagnostic test can be used for monitoring by comparison of the intra-individual variability metrics to a baseline over time, e.g., to detect changes over time. The quantified changes over time can then be used to determine a patient's estimated recovery trajectory or derived information such as return-from-disability date, return-to-duty date, or other time-based parameter.

It should now be apparent that the present invention provides a non-invasive system and method for simple, quantitative screening for mTBI using a submaximal grip test responsive to visual dynamic target-tracking to measure the variability of performance metric under predictable and unpredictable conditions, the metric serving as an initial screen of patients with mild traumatic brain injury (mTBI), and other neurological disorders.

The system and method can be administered by any level of caregiver, in any environment including military field deployments, and is useful in screening those truly injured from those disguising or mimicking injury.

Although the above-described invention is described in the context of an mTBI screen, one skilled in the art should understand that the screen is applicable to other forms of cognitive impairments including aging, Alzheimer's disease, progressive mental deterioration, senility, dementia, brain disease or injury, depression, alcohol or drug intoxication, etc. For example, the hand dynamometer may be configured to output its digital grip force data directly to a mobile computing device (e.g. mobile phone, tablet computer or stand-alone device).

Figure 8:
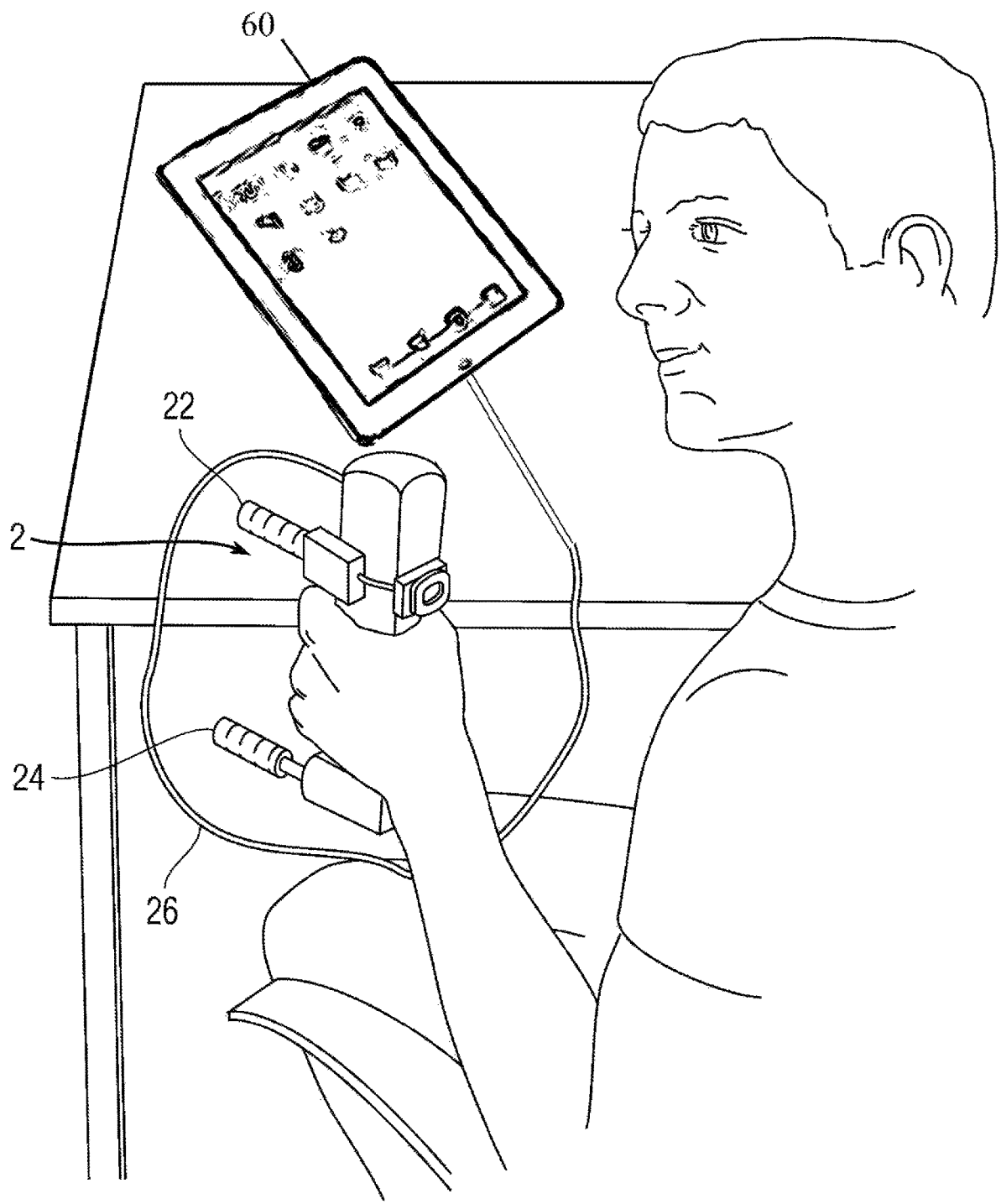
FIG. 8 shows a system for quantitative screening for cognitive impairment according to another embodiment of the present invention implemented with a tablet computer 60.

FIG. 8 shows a system for quantitative screening for cognitive impairment according to another embodiment of the present invention implemented with a tablet computer 60. The dynamometer 2 is connected in communication with the tablet computer 60 via existing data transfer port, or wirelessly by Bluetooth or other wireless network. In this instance, the data acquisition unit 32 is consolidated in software form in the tablet 60 (this consolidation is likewise possible with desktop computer 30), and the two become a single unit.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

INDUSTRIAL APPLICABILITY

There is a significant industrial need to screen individuals for mild cognitive impairment to ensure that they are capable of performing certain tasks safely without risk to themselves or others, or that a degenerative condition does not exist. The present invention fulfills this need with a method and system for administering a submaximal grip test using a hand dynamometer connected to a computer, and software that graphically guides an individual through two experimental visuomotor tasks: 1) tracking a predictable visual target; and 2) tracking an unpredictable visual target, both measuring the individual's fine visuomotor tracking accuracy in response to a stimulus on a computer screen. The system and method has great utility for initial screening, and ongoing baseline comparison of individuals showing signs of dysfunction from mTBI, and can potentially be used for screening other cognitive impairments such as brain damage, concussion, dementia, sleep deprivation, intoxication and the like.

What is claimed is:

1. A system comprising:
   a dynamometer configured to be gripped by a user and to be moveable by the user or to be tapped by the user, wherein the dynamometer comprises a transducer that generates a digital signal comprising output data related to grip strength or tap strength;
   a computer in communication with the dynamometer, wherein the computer comprises:
   a computer display,
   non-transitory computer memory storing computer readable instructions, and
   a programmable controller that accesses the non-transitory computer memory and executes the computer readable instructions to at least:
   displaying display on the computer display a graphical user interface comprising a moving visual target and a movable icon,
   move the visual target in at least one predictable moving pattern across the computer display at a predictable rate,
   receive a predictable digital signal output by the transducer of the dynamometer comprising predictable output data as the user grips the dynamometer with different forces to trace the visual target in the at least one predictable moving pattern with the moveable icon;
   determine a predictable metric value based on the predictable digital signal output,
   move the visual target in at least one unpredictable moving pattern across said computer display,
   receive an unpredictable digital signal output by the transducer of the dynamometer comprising unpredictable output data as the user grips the dynamometer with different forces to trace the visual target in the at least one unpredictable moving pattern with the moveable icon,
   determine an unpredictable metric value based on the unpredictable digital signal output,
   calculate an intra-individual variability of visuomotor tracking accuracy based on combining the predictable metric value and the unpredictable metric value, and
   compare the intra-individual variability of visuomotor tracking accuracy to a threshold to determine a likelihood that said user is suffering from mild cognitive impairment, and
   output onto the computer display a screening indicator representing the likelihood that the user is suffering from mild cognitive impairment,
   wherein the screening indicator is used to diagnose a cognitive impairment of the user.

2. The system according to claim 1, wherein the unpredictable metric and/or the predictable metric are based on a simple reaction time (SRT) by which grip force is adjusted by said user in reaction to movement of the target.

3. The system according to claim 1, wherein the unpredictable metric and/or the predictable metric are based on error correction by which grip force is readjusted by said user in reaction to movement of the target.

4. The system according to claim 1, wherein the unpredictable metric and/or the predictable metric are based on grip force variability over time.

5. A method comprising the steps of:
providing a dynamometer configured for being gripped by a user and to be moveable by the user or being tapped by the user, wherein the dynamometer comprises a transducer that generates a digital signal comprising grip-strength data or tap strength data indicative of sensory-motor feedback control requiring executive function via a visuomotor response;
providing a computer user interface comprising a visual target and a visual stimulus positionable on said computer user interface by association with the grip strength data or tap strength data;
moving, by a computer device associated with the computer user interface, the visual target across the computer user interface in an unpredictable moving pattern, wherein the unpredictable moving pattern comprises an unpredictable rate of movement along an irregular unpredictable path;
receiving, by the computer device, the digital signal corresponding to a grip of the user as the visual stimulus follows the visual target;
determining an intra-individual variability of visuomotor tracking accuracy over time during said unpredictable moving pattern to provide a first measure of sensory motor feedback control as a function of visuomotor tracking accuracy;
comparing the intra-individual variability to a threshold to determine a likelihood that said user is suffering from mild cognitive impairment; and
outputting a screening indicator onto the computer user interface representing the likelihood that said user has an increased risk of mild cognitive impairment.

6. The method according to claim 5, wherein the transducer comprises a load cell transducer for outputting the grip strength data.

7. The method according to claim 5, wherein the visual stimulus is a user-positionable icon controlled by said dynamometer.

8. The method according to claim 7, further comprising moving the visual target in a predictable pattern on the computer user interface.

9. The method according to claim 5, wherein the intra-individual variability of visuomotor tracking accuracy is based on a simple reaction time (SRT) of the user.

10. The method according to claim 5, wherein the intra-individual variability of visuomotor tracking accuracy is based on a measured error correction value.

11. The method according to claim 5, wherein the intra-individual variability of visuomotor tracking accuracy is based on grip strength data variability.

* * * * *